United States Patent [19]
Glantz

[11] Patent Number: 5,749,835
[45] Date of Patent: May 12, 1998

[54] METHOD AND APPARATUS FOR LOCATION OF A CATHETER TIP

[75] Inventor: Jerald Glantz, Lake Elmo, Minn.

[73] Assignee: SIMS Deltec, Inc., St. Paul, Minn.

[21] Appl. No.: 782,518

[22] Filed: Jan. 9, 1997

Related U.S. Application Data

[63] Continuation of Ser. No. 644,734, May 10, 1996, abandoned, which is a continuation of Ser. No. 301,869, Sep. 6, 1994, abandoned.

[51] Int. Cl.$^6$ .................................................. A61B 5/05
[52] U.S. Cl. .................................................. 600/424
[58] Field of Search .................................. 128/653.1, 654, 128/656–658, 897, 899, 903; 324/207.11, 207.17, 207.28; 600/11–14, 125, 117, 407, 431, 433–435, 424; 604/280

[56] References Cited

U.S. PATENT DOCUMENTS

| | | | |
|---|---|---|---|
| 4,756,708 | 7/1988 | Martin | 604/283 |
| 4,844,092 | 7/1989 | Rydell et al. | 128/657 |
| 4,905,698 | 3/1990 | Strohl, Jr. et al. | |
| 4,973,329 | 11/1990 | Park et al. | 128/657 |
| 5,062,836 | 11/1991 | Wendell | 604/167 |
| 5,099,845 | 3/1992 | Besz et al. | 128/653.1 |
| 5,253,647 | 10/1993 | Takahashi et al. | 128/653.1 |
| 5,273,025 | 12/1993 | Sakiyama et al. | 128/899 |
| 5,325,873 | 7/1994 | Hirschi et al. | 128/653.1 |
| 5,338,296 | 8/1994 | Dalessandro et al. | |
| 5,357,961 | 10/1994 | Fields et al. | 128/658 |
| 5,360,407 | 11/1994 | Leonard | |
| 5,386,828 | 2/1995 | Owens et al. | 600/13 |
| 5,425,367 | 6/1995 | Shapiro et al. | 128/653.1 |
| 5,429,132 | 7/1995 | Guy et al. | 128/653.1 |
| B1 4,905,698 | 10/1991 | Strohl, Jr. et al. | |

FOREIGN PATENT DOCUMENTS

| | | |
|---|---|---|
| A 0 091 577 | 3/1983 | European Pat. Off. |
| A 0 320 623 | 6/1989 | European Pat. Off. |

OTHER PUBLICATIONS

*American Journal of Nursing*, article entitled: "The Hickman Indwelling Catheter," by Joan Bjeletich and Robert O. Hickman, Jan. 1980.

Published bibliographic information about K895712 from a DIOGENES® publication dated 1990.

Copy of the full Sectiion 510(K) Notification records for K895712 as released to the public.

*Primary Examiner*—Brian L. Casler
*Attorney, Agent, or Firm*—Merchant, Gould, Smith, Edell, Welter & Schmidt P.A.

[57] ABSTRACT

The present invention relates to a method and apparatus used to place a catheter having a distal end and a proximal end where the proximal end cannot be trimmed within a patient. The method and apparatus utilize a device operative in locating the tip of a catheter, which includes a detector assembly having a detector and a locator. The detector of the detector assembly is locked into positioned remote from the distal end of the catheter prior to inserting the catheter in the patient. The distal end of the catheter is trimmed, as to define a trimmed distal end, the detector is then unlocked and placed proximate the trimmed end. In the preferred embodiment the detector is locked into place proximate the trimmed distal end and the catheter is placed within the patient.

12 Claims, 8 Drawing Sheets

METHOD AND APPARATUS FOR LOCATION OF A CATHETER TIP

This is a File Wrapper Continuation of application Ser. No. 08/644,734, filed May 10, 1996 now abandoned, which is a Filed Wrapper Continuation of application Ser. No. 08/301,869, filed Sep. 6, 1994, now abandoned.

FIELD OF THE INVENTION

The present invention relates to methods and apparatus for locating the tip of a catheter positioned in biological tissue.

BACKGROUND

The treatment of certain diseases often requires infusion of drugs or medicants into the body. When infusing such medicants, a caregiver will often make a venipuncture with a cannula to access a vein, and thread a catheter through the vein to a desired location. The catheter includes a distal end, a proximal end and one or more lumens therebetween. The distal end of the catheter may be placed at a variety of locations including the superior vena cava. The proximal end of the catheter is then coupled to a portal within the body or passes exterior of the body.

Generally, portals are sealed reservoirs accessible through a septum. The portal is connected to the proximal end of the catheter and subcutaneously implanted within the patient. Catheters which pass external of the body include: PICC (Peripherally Inserted Central Catheter) catheters, which access the superior vena cava through the cephalic vein in the arm; and chest catheters (often referred to as Hickman catheters) which pass through a tunnel bored into the chest then into the cephalic vein.

The prior art provides for methods and devices to locate the distal end of the catheter within the body as the catheter is inserted into the vein. For example, commonly assigned U.S. Pat. No. 4,905,698 to Strohl et al describes a method and apparatus for catheter location determination. The method and apparatus of Strohl utilizes a source which generates an alternating magnetic field, and a detector positioned proximate the distal end of the catheter. The detector generates a voltage in response to the proximity of the field generated by the source. The phase of the voltage in the detector shifts as the source passes over it. By referencing anatomical landmarks at the time the phase shift occurs, the caregiver can determine the exact location of the detector, and thus the location of the tip of the catheter.

The method and apparatus of Strohl are advantageous because the tip of the catheter can be located without use of fluoroscopy. Fluoroscopy involves using x-rays to locate the distal end of the catheter.

After the catheter is implanted, medicants are delivered therethrough to the desired location. Medicants are introduced either directly into the catheter, as in the case of a PICC catheter or chest catheter, or through bolus injection or continuous infusion into the portal. Each technique for delivering medicants has associated advantages which a caregiver evaluates in determining how medicants will be delivered to a patient.

In the prior art, catheters are sold in predetermined lengths. Often, the length of the catheter purchased does not meet the exact needs of the patient. In the case of catheters used in conjunction with portals, the caregiver positions the distal end of the catheter within the patient, for example at the superior vena cava, and trims the proximal end so that the catheter is the proper length. This is especially necessary when the length of the catheter is greater than the distance between the superior vena cava and the location of the portal. The distal end will be located, and the proximal end will be trimmed prior to connection with the portal.

If the device of Strohl has been used to locate the distal end of the catheter, in connection with placement of a portal, the caregiver will remove the device of Strohl prior to trimming the proximal end of the catheter. The device of Strohl is removed by disconnecting a coupling positioned on an associated junction box. The caregiver then trims the proximal end of the catheter, fits the portal to the proximal end of the catheter and places the portal within the patient.

Chest type and PICC catheters are also sold in predetermined lengths which do not often meet the needs of the patient. To place a chest or PICC catheter the caregiver would lay the catheter over the patient to determine the proper length and trim the distal end. The catheter would then be placed using fluoroscopy.

In the prior art, use of devices of the type described in Strohl U.S. Pat. No. 4,905,698 are not used with either chest or PICC type catheters. Use of these devices in the prior art are limited to use with portals. In particular, the device of Strohl is secured within the lumen of the catheter so that the detector of Strohl is positioned at the distal end of the catheter. When the distal end of the catheter has been located the proximal end is trimmed. Both PICC and chest catheters include permanent fittings on their proximal ends which cannot be trimmed. The device and method taught by Strohl cannot be used with catheters which include fittings at the proximal end, such as PICC catheters or chest catheters, because the proximal end of the catheter cannot be trimmed. Therefore, a need has arisen to provide an apparatus and method which permits the safe and convenient use of the device of Strohl or other related devices with PICC and chest catheters.

SUMMARY OF THE INVENTION

The present invention provides a method for determining the location of a tip of a catheter located in biological tissue. The catheter includes a distal end, a proximal end, and a lumen positioned therebetween. The method includes providing a source which develops an external alternating magnetic field, to locate a detector, which is operable in generating a voltage when the source is proximate the detector. The detector is locked remote from the distal end of the lumen of the catheter.

The method further includes the steps of trimming the distal end of the catheter. The detector is then unlocked from within the lumen of the catheter and positioned proximate the trimmed distal end of the catheter. The catheter is then positioned within the biological tissue and the source is placed proximate the detector to locate the trimmed distal end of the catheter.

The present invention also provides a catheter for use with a catheter tip location device. The catheter includes a proximal end, a distal end, and a lumen positioned therebetween, while the catheter tip location device includes a source providing an alternating magnetic current and a detector positioned within the lumen of the catheter. The catheter tip location device is operable in detecting the position of the detector positioned within the lumen of the catheter. A lock is positioned at the proximal end of the catheter, the lock being selectively movable among a variety of locked positions, the lock operable in selectively locking the detector remote from the distal end in any position chosen by the caregiver or manufacturer.

DETAILED DESCRIPTION OF THE PREFERRED EMBODIMENTS

The present invention is directed toward a method and apparatus for placing a chest catheter or PICC catheter within a patient. The catheter includes a distal end, a proximal end, and at least one lumen positioned therebetween. The proximal end of the catheter includes a lock fitting. The method involves the steps of providing a catheter having a lumen and a detector locked within the lumen of the catheter where the detector is positioned remote from the distal end of the catheter. The detector is operable in generating a voltage when a source is proximate the detector.

The catheter is placed external to the body as to determine the proper length of the catheter. The distal end of the catheter is trimmed to the proper length, and then the detector is unlocked from within the lumen of the catheter. The detector is then repositioned proximate to the trimmed distal end of the catheter and locked in place using the lock fitting. After the detector is repositioned, the catheter is positioned within the biological tissue and the source is placed proximate the detector to locate the trimmed distal end of the catheter.

Figures 1, 2:
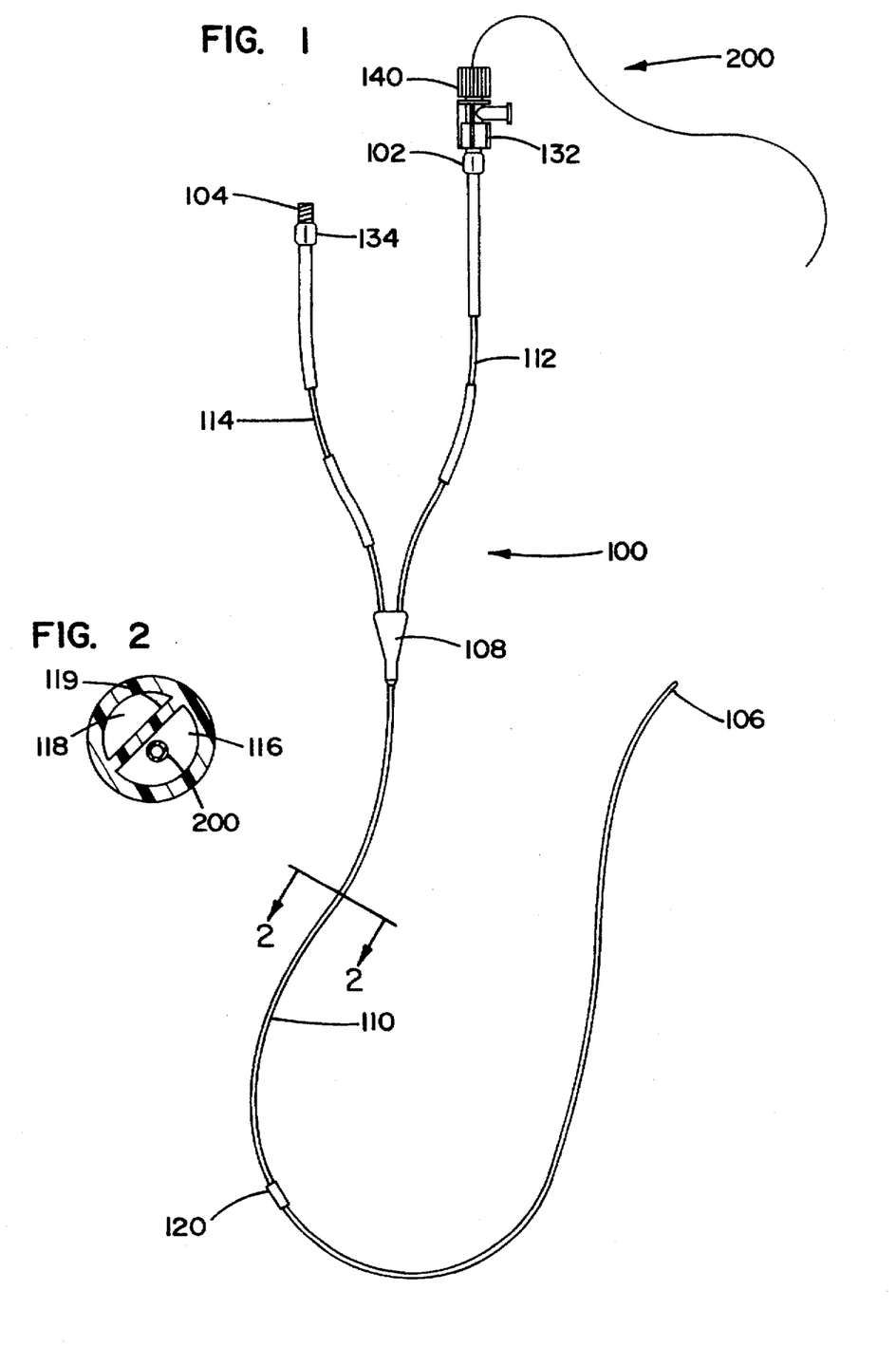
FIG. 1 is a front view of a dual lumen chest catheter.
FIG. 2 is a cross-sectional view of the chest catheter taken along the line 2—2.
Figure 6:
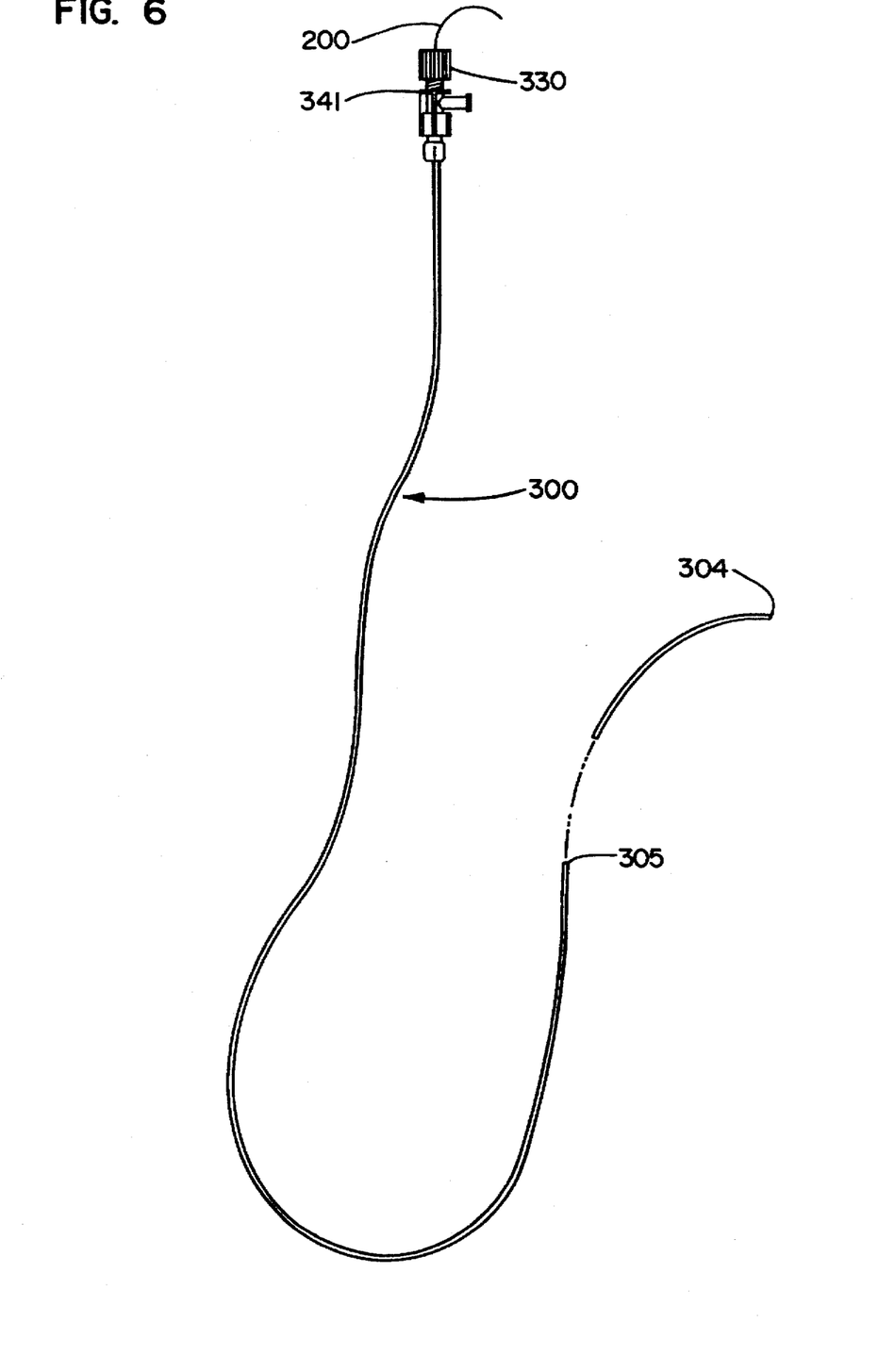
FIG. 6 is a front view of a PICC catheter having its distal end trimmed.

Referring now to the Figures in which like elements are numbered alike, the present invention is shown. The catheter shown in FIG. 1 is a dual lumen chest catheter, while the catheter shown in FIG. 6 is a PICC catheter. A significant difference in structure between the chest catheter of FIG. 1 and the PICC catheter of FIG. 6 is dimension and the number of lumens each may contain. For example, the greater diameter of the chest catheter shown in FIG. 1 permits the multiple lumens disclosed in FIG. 2. However, the method and apparatus of the present invention is not precluded from use in multi-lumen PICCs.

With initial reference to FIG. 1, there is shown a catheter 100 having a first proximal end 102, a second proximal end 104 and a distal end 106. Catheter 100 of the first preferred embodiment includes three portions, which are connected by a Y shaped member 108. Generally these portions are a lower portion 110 and two pigtail portions 112, 114.

Lower portion 110 of catheter 100, as shown in FIG. 2, includes a first lumen 116 and a second lumen 118 separated by a septum 119. First lumen 116 connects distal end 106 to a first pigtail and first proximal end 102 and second lumen 116 connects distal end 106 to second pigtail and second proximal end 104. In one preferred embodiment, first lumen 116 has a larger lumen than that of second lumen 118.

Figure 4:
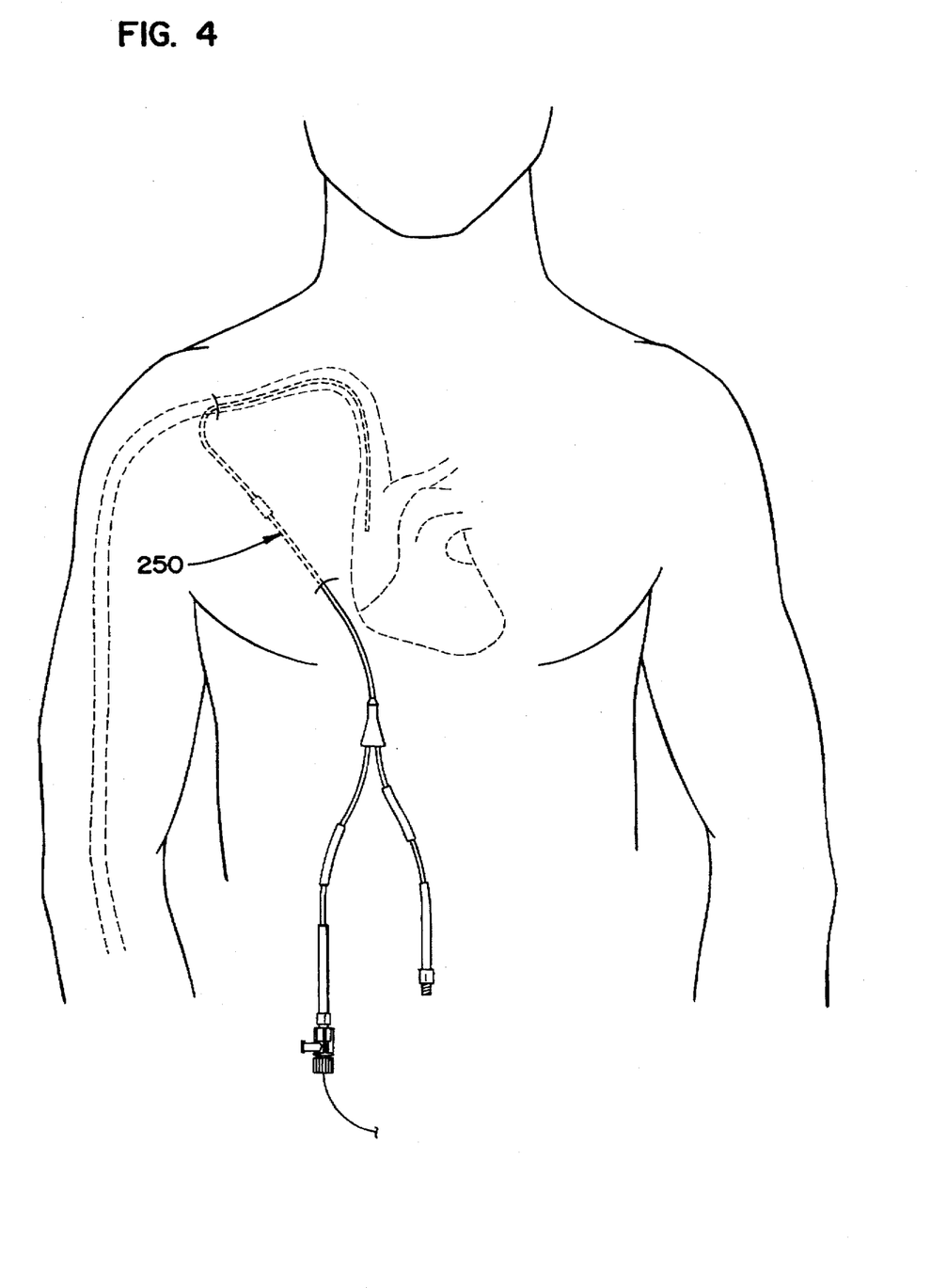
FIG. 4 is a front view of a patient with the chest catheter of FIG. 3 in place prior to removal of a detector.

Positioned on lower portion 110 between Y member 108 and distal end 106 is a cuff 120. Preferably, cuff 120 is constructed from Dacron, a registered trademark of E. I. Dupont De Nemours. (Dacron is a polyester fiber typically made from polyethylene terephthalate.) Cuff 120 functions to anchor catheter 100 within the biological tissue after placement. Specifically, and with reference to FIG. 4, there is shown a chest catheter, which when implanted within a patient passes through a tunnel 250 bored within the chest of the patient. Catheter 100 is anchored by the biological tissue surrounding cuff 120 in tunnel 250 which grows into cuff 120. Cuff 120 then assists in preventing infection within the patient.

Figure 3:
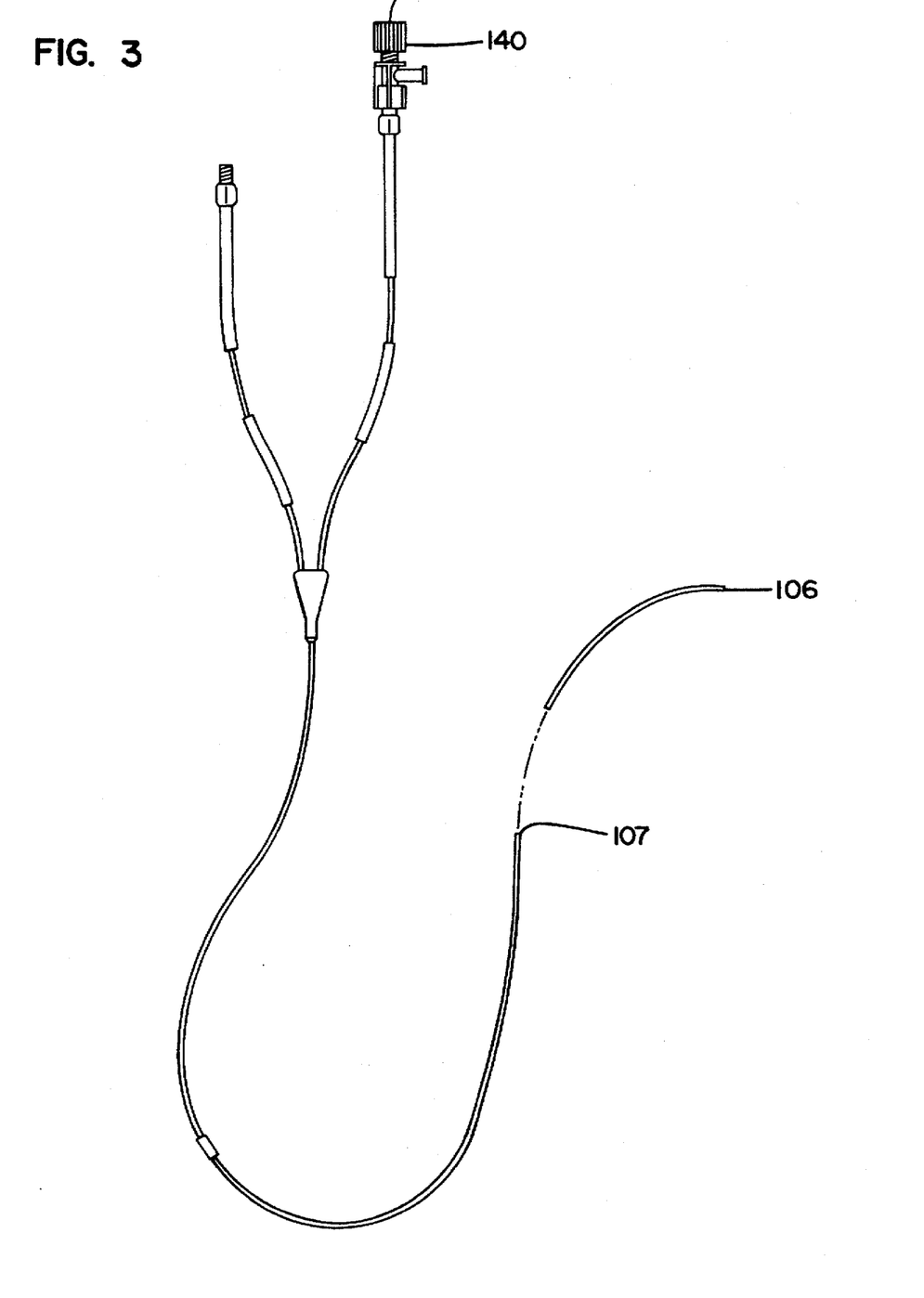
FIG. 3 is a front view of the catheter shown in FIG. 1 showing its distal end being trimmed.

Referring to FIGS. 1 and 3, a pair of fittings 132 and 134 are attached to first and second proximal ends 102, 104 of catheter 100, respectively. Fittings 132 and 134 facilitate connection of catheter 100 to other medical devices, such as an infusion pump (not shown), which operates to deliver medicants through catheter 100 to the superior vena cava, for example.

In the first preferred embodiment of the present invention, a locking fitting 140 is attached to first proximal end 102 of catheter 100 at fitting 132. Locking fitting 140 is preferably a locking hemostasis type valve which includes an aperture which decreases in size in response to twisting the valve. Hemostasis type valves ordinarily are used to prevent blood flow out of the patient through the catheter. Specifically, locking fitting 140 operates to lock a detector assembly 200, of an apparatus for locating the tip of the catheter, into place. The apparatus for locating the tip of the catheter is of the type described in commonly assigned U.S. Pat. No. 4,905,698 the disclosure of which is fully incorporated herein by reference.

Figure 5:
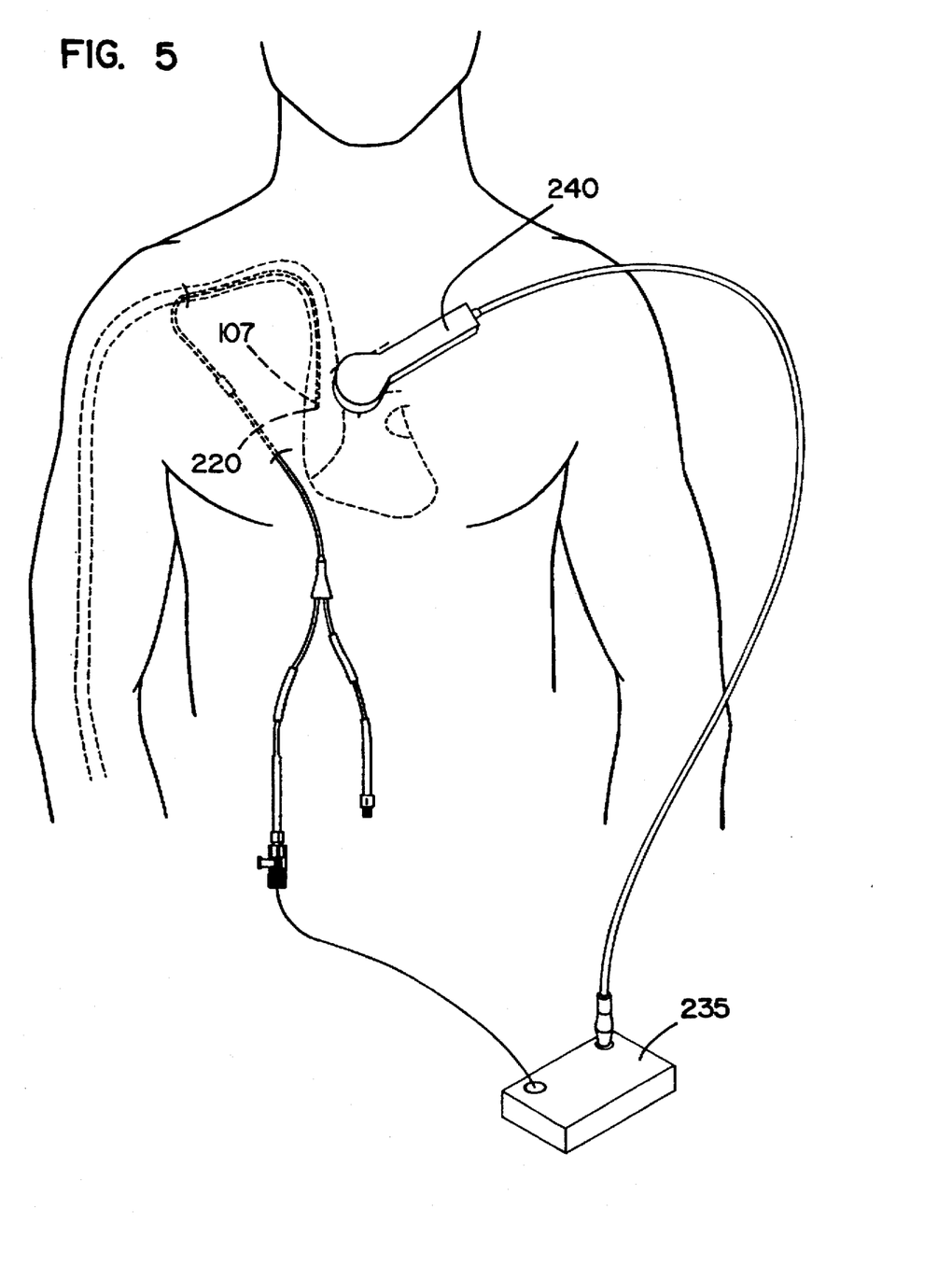
FIG. 5 is a front view of a patient with the chest catheter of FIG. 3 in place, with a device operative in locating the tip of the catheter in use.
Figure 7:
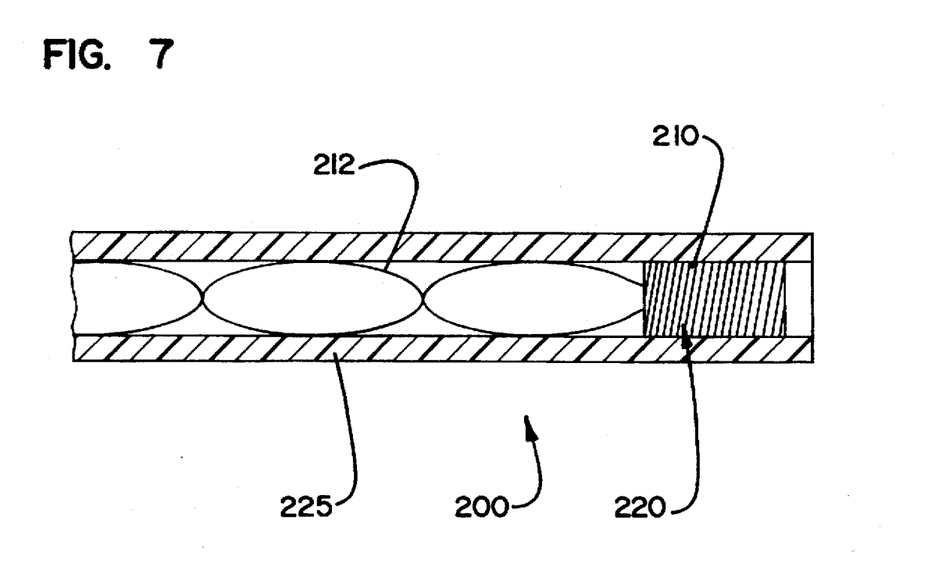
FIG. 7 is a cross sectional view of a detector assembly operative in locating the tip of a catheter.

Referring to FIGS. 5 and 7, detector assembly 200 generally includes a detector 220 which has a magnetic core 210 wrapped by a wire 212. Wire 212 includes a first end and a second end both of which are connected to an electronic controller 230. Magnetic core 210 including wire 212 which is wrapped therearound is generally referred to as detector 220. The detector assembly 200, as described in U.S. Pat. 4,905,698, is located in hollow jacket 225, while the detector is located at the tip of the hollow jacket.

In the preferred embodiment of the present invention detector assembly 200 is locked within first lumen 116 of lower portion 110 of catheter 100 proximate cuff 120. Detector assembly 200 is locked into position by locking fitting 140. In the first preferred embodiment, detector assembly 200 passes through locking fitting 140, which operates to capture hollow jacket 225 of detector assembly 200.

As shown in FIG. 3 fittings 130 and 132 are positioned on the proximal ends 102 and 104 of catheter 100. Because fittings 130 and 132 are positioned on proximal ends 102 and 104 of catheter 100, a caregiver cannot first place catheter 100 and then trim the excess catheter length off of the proximal end as taught by the prior art. In the present invention, the caregiver first lays catheter 100 on the patient to determine the approximate length of catheter 100 necessary for the specific patient. The proper length is determined by the caregiver through reference to anatomical landmarks on the patient.

The caregiver then trims distal end 106 of catheter 100, as to define a trimmed distal end 107, as shown in FIG. 3 so that it is the proper length. Once catheter 100 is trimmed to the proper length, the caregiver can loosen locking fitting 140 and reposition detector 220 of detector assembly 200 at trimmed distal end 107 of catheter 100.

The catheter can then be placed into the biological tissue using the techniques of commonly assigned U.S. Pat. No. 4,905,698, which has been previously incorporated by reference. The method and apparatus described in U.S. Pat. No. 4,905,698 involves the use of detector 220, a source, shown as 235 in FIG. 5, and a locator 240. Source 235 generates an alternating magnetic field which is placed proximate detector 220 by a locator 240. Detector 220 generates a voltage in response to the magnetic field when locator 240 is proximate detector 220. As stated above, detector is positioned proximate trimmed distal end 107 of catheter 100. The phase of the voltage generated by detector 220 shifts as locator 240 passes over it. By referencing anatomical landmarks at the time the phase shift occurs, the caregiver can determine the location of detector 220, and thus the location of trimmed distal end 107 of catheter 100.

Once the trimmed distal end 107 of catheter 100 is placed, and located, locking fitting 140 is loosened and detector assembly 110 is removed. Detector assembly is removed by pulling it through lumen 116 of catheter 100.

Figure 5A:
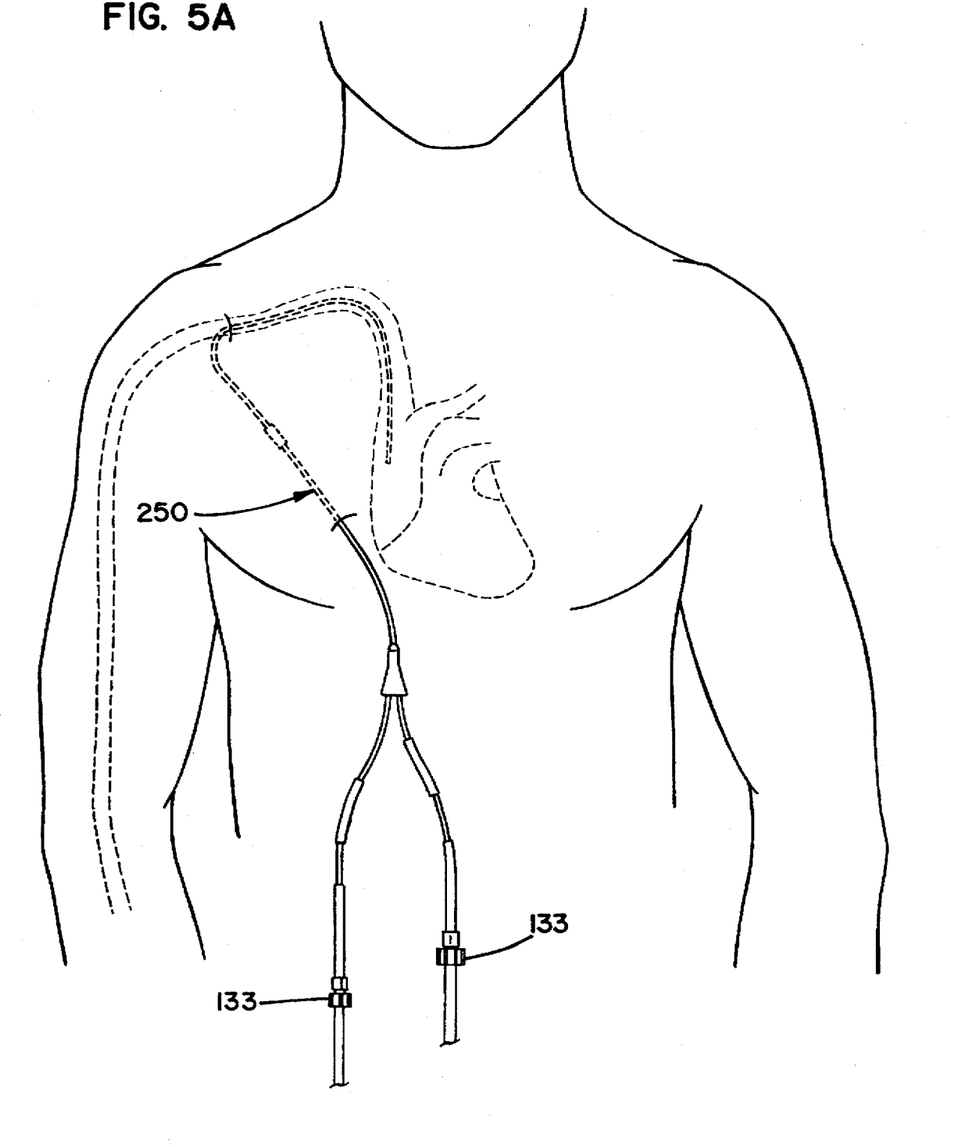
FIG. 5A is a front view of a patient with the chest catheter of FIG. 1, with the catheter in operation.

As shown in FIG. 5A, fittings 130 and 132 may each then be connected to a mating fitting 133 from a pump (not shown) or another catheter (not shown). In this fashion medicants may be delivered through the catheter to the patient.

It is to be understood that the above described method and construction is intended for use with any catheter, regardless of how many pigtail ends, which has a fitting or other structure on its proximal end and therefore prohibits the trimming of its proximal end after placement. Further, it is to be understood that the above-described method includes alternate methods of catheter tip location which include insertion or removal of a detector.

Figure 6A:
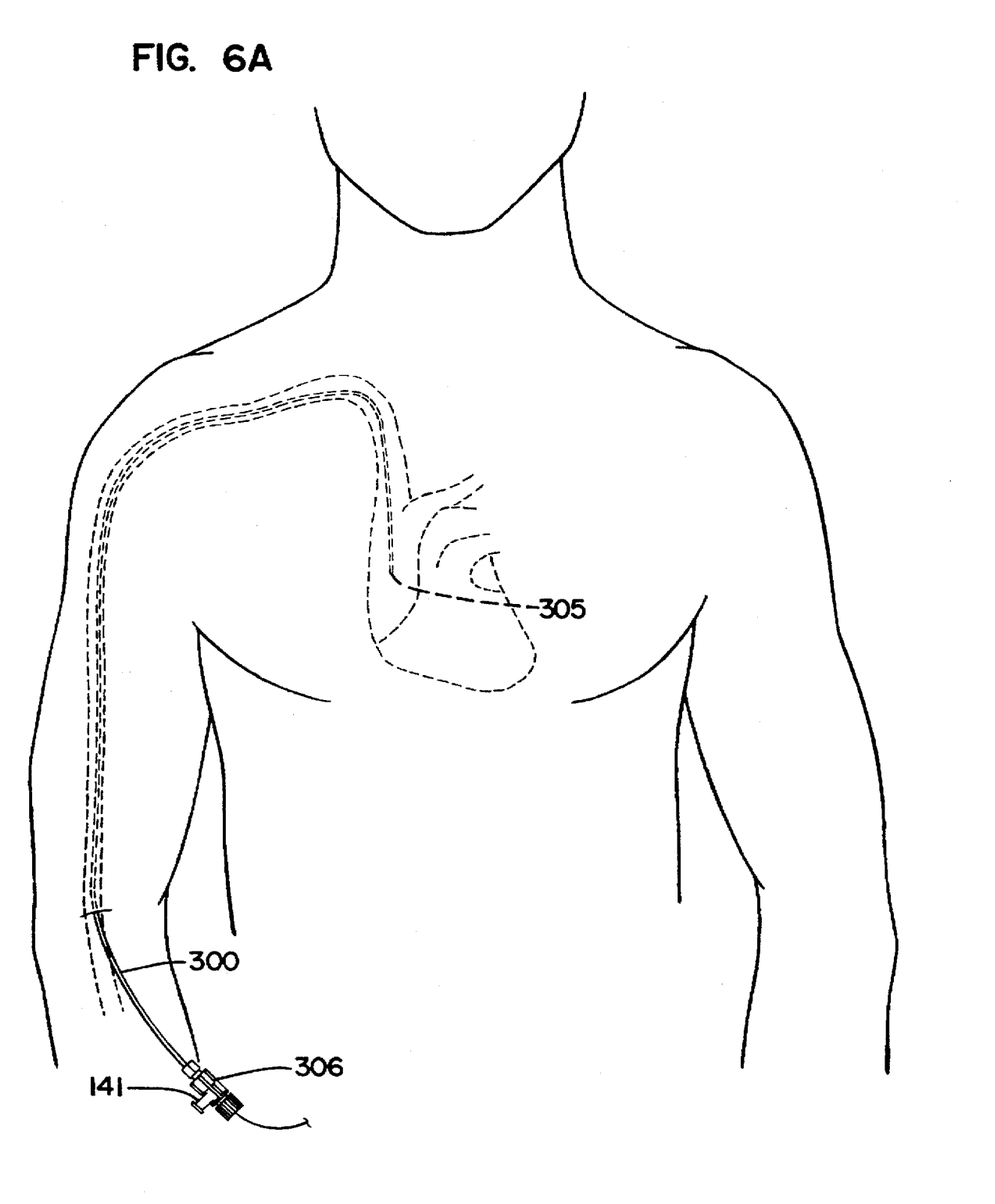
FIG. 6A is a front view of a patient with the PICC catheter of FIG. 6 in place, prior to removal of the detector.

With reference to FIGS. 6 and 6A, an example of a second type of catheter which includes a fitting at its proximal end is shown. Specifically, the catheter shown in FIG. 6 is a PICC catheter 300. PICC catheter 300 accesses the cephalic vein proximate the arm of the patient and travels therethrough to the superior vena cava, where medicants may be delivered. As above, PICC catheter 300 includes a detector assembly 200 placed within its lumen, not separately shown, with detector 220 of detector assembly 200 positioned distal from the distal end of PICC catheter 300.

Generally, and with reference to FIG. 6, PICC catheter 300 does not include pigtails as the diameter of the lumen of PICC catheter 300 is too small. PICC catheter 300 includes a distal end 304 having a fitting 330 and a proximal end 306. To place PICC catheter 300 using the method of the present invention, a caregiver places PICC catheter 300 over the patient to estimate the approximate length of PICC catheter 300, in a fashion similar to that described above. As shown in FIG. 6, the caregiver then trims distal end 304 as to define a trimmed distal end 305 of PICC catheter 300.

Once the distal end of PICC catheter 300 has been trimmed, a locking fitting 341, preferably a locking hemostasis type valve, may be loosed and detector 220 of detector assembly 200 may be placed proximate trimmed distal end 305 of PICC catheter 300. PICC catheter 300 may then be placed using the method taught in U.S. Pat. No. 4,905,698 to Strohl, previously incorporated by reference.

The present invention includes significant advantages over the prior art. These advantages include minimization of steps necessary in positioning a catheter. Minimization of the steps reduces the opportunity for error to occur. Errors which may occur in the placement of the catheter include cutting the detector assembly and unnecessary placement of catheters which have an improper length.

Additionally, PICC type catheters which travel a relatively great distance within the body can now be tracked using the non-intrusive method taught by U.S. Pat. No. 4,905,698 to Strohl. This is a significant advantage in view of the various body pathway "intersections" which a PICC type catheter must pass, on its way to the superior vena cava, in which the catheter can deviate from its intended path during placement. If such deviation goes unchecked it can result in delivering much needed medicants to the wrong location.

While the foregoing detailed description of the present invention describes the invention of the preferred embodiments, it will be appreciated that it is the intent of the invention to include all modifications and equivalent designs. Accordingly, the scope of the present invention is intended to be limited only by the claims which are appended hereto.

What is claimed is:

1. A method for determining the location of a tip of a catheter, inside biological tissue, wherein the catheter includes a distal end and a proximal end and a lumen positioned therebetween, the method comprising the steps of:
   a) providing a source;
   b) providing a detector locked within the lumen of the catheter remote from the distal end of the catheter, the detector operable in generating a voltage when the source is proximate the detector;
   c) trimming the distal end of the catheter as to define a trimmed distal end;
   d) unlocking the detector from within the lumen of the catheter;
   e) positioning the detector proximate the trimmed distal end of the catheter;
   f) positioning the trimmed distal end of the catheter within the biological tissue; and
   g) placing the source proximate the detector to locate the trimmed distal end of the catheter.

2. A method as in claim 1 wherein said source is operative in generating an external alternating magnetic field.

3. A method as in claim 1 further comprising the step of locking the detector proximate the trimmed distal end of the catheter after positioning the detector proximate the distal end of the catheter.

4. A method as in claim 3 further comprising the steps of unlocking the detector and removing the detector.

5. A method as in claim 4, wherein the catheter includes a fitting at a proximal end, the method further comprising the step of connecting a mating fitting to the fitting.

6. A catheter detection system, comprising:
   a) a catheter including a proximal end, a distal end, and a lumen positioned therebetween;
   b) a catheter tip location device including a source providing an alternating magnetic current and a detector positioned within the lumen of the catheter; the catheter tip location device operable in detecting the position of the detector positioned within the lumen of the catheter; and
   c) a lock positioned at the proximal end of the catheter, the lock being selectively movable between a locked position and an unlocked position, the lock selectively locking the detector remote from the distal end.

7. A catheter detection system as in claim 6 wherein the proximal end of the catheter includes a fitting.

8. A catheter detection system as in claim 6 wherein the lock comprises a locking hemostasis valve.

9. A catheter detection system as in claim 6 wherein the catheter includes a single distal end and multiple proximal ends, and multiple lumens therebetween, each of the multiple proximal ends including a fitting.

10. A catheter detection system as in claim 6 wherein the catheter is a chest-type catheter.

11. A catheter detection system as in claim 6 wherein the catheter is a peripherally inserted central catheter.

12. A catheter comprising:
a) a catheter body including a proximal end, a distal end, and a lumen positioned therebetween;
b) a catheter detector positioned within the lumen of the catheter remote from the distal end of the catheter; and
c) a lock positioned at the proximal end of the catheter, the lock being selectively movable between a locked position and an unlocked position, the lock operable in selectively locking the detector remote from the distal end, the lock locking the detector at the remote location.

* * * * *